US00PP18241P2

(12) United States Plant Patent
Sanders

(10) Patent No.: US PP18,241 P2
(45) Date of Patent: Nov. 20, 2007

(54) ***IMPATIENS* PLANT NAMED 'IMDOSAOR'**

(50) Latin Name: *Impatiens walleriana*
Varietal Denomination: Imdosaor

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/438,044
(22) Filed: May 19, 2006
(51) Int. Cl.
*A01H 5/00* (2006.01)

(52) U.S. Cl. ..... Plt./317
(58) Field of Classification Search ..... Plt./317
See application file for complete search history.

(56) References Cited

U.S. PATENT DOCUMENTS

PP9,691 P * 11/1996 Leue ..... Plt./317

OTHER PUBLICATIONS

UPOV ROM GTITM Computer Database, GTI Jouve Retrieval Software 2006/04 Citations for 'Imdosaor'.*

* cited by examiner

*Primary Examiner*—Wendy C. Haas
(74) *Attorney, Agent, or Firm*—Bruce Vrana

(57) ABSTRACT

A new *Impatiens* plant, characterised particularly as to novelty by an upright habit, freely branching, with large, double, salmon orange flowers, flowering above the foliage.

1 Drawing Sheet

Latin name of the genus and species of the plant claimed: *Impatiens walleriana.*
Varietal denomination: 'Imdosaor'.

BACKGROUND OF THE NEW PLANT

The present invention comprises a new distinct cultivar of *Impatiens,* botanically known as *Impatiens walleriana.*

The new *Impatiens* is a product of a planned breeding program conducted in Enkhuizen, Netherlands. The new *Impatiens* cultivar is upright growing, early flowering, floriferous with large, double flowers and has attractive foliage.

The present cultivar originated from a pollination made in 2001, of a proprietary *Impatiens* selection identified as 'S3244-1,' not patented, as the female, or seed parent, with a proprietary *Impatiens* selection identified as 'S3163-1,' , not patented, as the male, or pollen parent.

The present cultivar has been repeatedly asexually reproduced by cuttings in Enkhuizen, Netherlands, in Angers, France, in Gilroy, USA over a four year period. The distinctive characters of this new *Impatiens* are stable and reproduced true to type in successive generations of asexual reproduction. It takes 6 to 8 weeks to produce a finished plant, depending on the temperature.

This new *Impatiens* plant is an annual in most climatical zones in the US, only in zones 9 and 10 it is a perennial plant.

DESCRIPTION OF THE DRAWING

This new *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Impatiens.* The data which defines these characteristics were collected from asexual reproductions carried out in Enkhuizen, Netherlands. The plant history was taken on 25 week old plants, blossomed under natural light in the field.

Color readings were taken in the office under ambient light. Color references are primarily to The R.H.S. Color Chart of The Royal Horticultural Society of London.

Plants of the new *Impatiens* differ primarily from the plants of the female parent selection in the following characteristics:

Plants of the new *Impatiens* have orange, double flowers and flowers only have petals, whereas the plants of the female have orange flowers and flowers have a pollen cap and stigma.

Plants of the new *Impatiens* differ primarily from the male plant selection in the following characteristics:

Plants of the new *Impatiens* have orange colored flowers, whereas the plants of the male have salmon colored flowers.

TABLE 1

DIFFERENCES BETWEEN THE NEW CULTIVAR 'IMDOSAOR' AND A SIMILAR CULTIVAR

| | 'Imdosaor' | 'Salmon Sunrise' (U.S. Plant Pat. No. 9,691) |
|---|---|---|
| Leaf color | Dark green | Medium green |
| Flower size | Large | Smaller |
| Number of petals | Very high number | Normal number |

Parentage:
*Female parent.*—'S3244-1,' not patented.
*Male parent.*—'S3163-1,' not patented.

Propagation:
*Type cutting.*—Terminal cuttings.
*Time to initiate roots.*—10–12 days at 20 degrees C.
*Time to produce a rooted cutting.*—4 weeks.
*Root description.*—Fine, fibrous and white in color.

Plant description:

*General appearance.*—Compact, mounded and outwardly spreading. Appropriate for 12 cm pots and large containers.

*Growth and branching habit.*—Upright growing plant habit, well branched.

*Crop time.*—6–8 weeks, starting from an unrooted cutting in a 10.5 cm pot.

*Plant height.*—12 cm.

*Plant diameter or spread.*—44.5 cm.

Lateral branches:

*Length.*—About 21 cm.

*Diameter.*—About 5 mm.

*Internode length.*—About 2 cm.

*Texture.*—Smooth.

*Color.*—146D.

*Anthocyanin may be present.*—59B.

Foliage description:

*Arrangement.*—Simple, alternate.

*Length.*—About 4.6 cm.

*Width.*—About 2.7 cm.

*Shape.*—Ovate.

*Apex.*—Acuminate.

*Base.*—Attenuate.

*Margin.*—Serrate, rounded.

*Texture.*—Glabrous, smooth.

*Venation pattern.*—Pinnate, arcuate.

*Color, developing and fully expanded foliage, upper surface.*—137A.

*Color, developing and fully expanded foliage, lower surface.*—147C.

*Venation, upper and lower surfaces.*—137C.

*Petiole, length.*—About 2.1 cm.

*Petiole, diameter.*—About 2 mm.

*Color.*—49D with green.

Flower description:

*Flower type and flowering habit.*—Numerous and consistently large fully double flowers. Freely and continuously flowering. Flower buds open similar to a rose in fullness; flowers rounded. Flowers arise from leaf axils. Typically about 24 flowers and flower buds per lateral branch. Flowers positioned above and beyond the foliage and typically face outward. Flowers last about five to seven days under greenhouse conditions. Flowers not persistent. Flowers not fragrant.

*Flowering season.*—Year round under greenhouse conditions. In the garden, flowering is continuous from Spring until Fall.

*Flower size.*—Diameter: About 4 cm. Depth: About 2 cm.

Flower buds:

*Length, at stage for showing color.*—About 1.2 cm.

*Diameter, at stage for showing color.*—About 10 mm.

*Shape.*—Ovoid.

*Color.*—55D.

Petals:

*Quantity/arrangement.*—About 40 per flower; imbricate.

*Length, outer petals.*—About 2.4 cm.

*Width, outer petals.*—About 1.9 cm.

*Shape.*—Oval to obovate.

*Apex.*—Emarginate to retuse.

*Base.*—Shortly attenuate.

*Margin.*—Entire.

*Texture, upper and lower surfaces.*—Velvety, smooth.

*Color.*—When opening, upper surface: 40A. When opening, lower surface: 43D. Fully opened, upper surface: 40A. Fully opened, lower surface: 43D.

Spurs:

*Length.*—About 2.3 cm.

*Color.*—N144D.

Sepals:

*Quantity/arrangement.*—Five in a single whorl.

*Calyx length.*—About 3 mm.

*Calyx diameter.*—About 2 mm.

*Shape.*—Elliptic.

*Apex.*—Acute.

*Margin.*—Entire.

*Texture, upper and lower surfaces.*—Smooth.

*Color.*—Upper surface: 145A. Lower surface: 145A.

Peduncles:

*Length.*—About 2.1 cm.

*Diameter.*—About 2 mm.

*Angle.*—About 45 degrees to the lateral branch.

*Strength.*—Moderately strong.

*Color.*—152C.

Reproductive organs: None observed.

Seed/fruit development: Seed and fruit development has not been observed.

What is claimed is:

1. A new and distinct cultivar of *Impatiens* plant named 'Imdosaor,' as substantially illustrated and described herein.

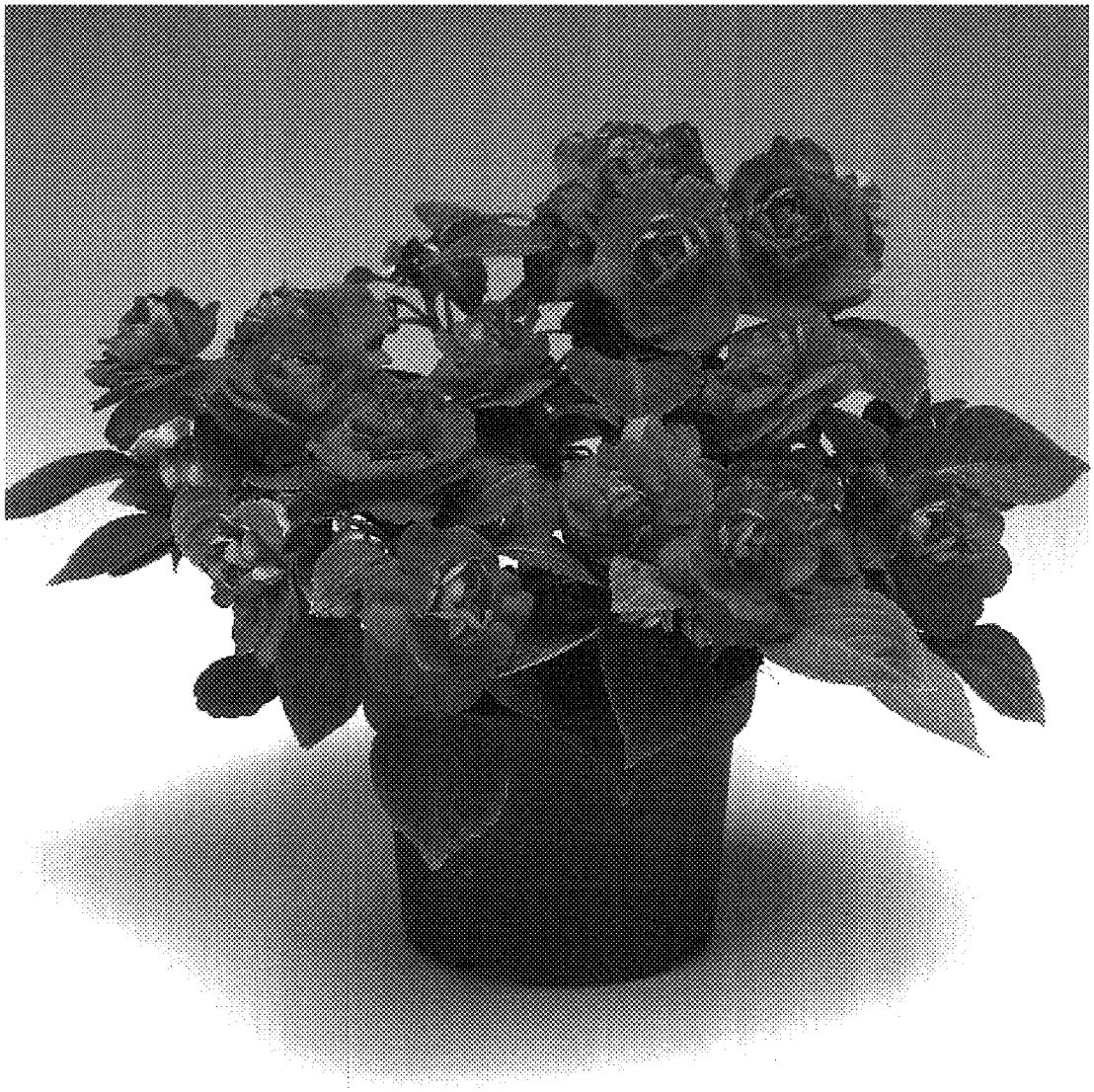

* * * * *